United States Patent [19]

Oda et al.

[11] 4,025,565

[45] May 24, 1977

[54] PROCESS FOR PREPARING UNSATURATED ALDEHYDE HAVING THREE TO FOUR CARBON ATOMS

[75] Inventors: Yoshio Oda; Keiichi Uchida, both of Yokohama; Manabu Suhara, Tokyo; Takeshi Morimoto, Yokohama, all of Japan

[73] Assignee: Asahi Glass Co., Ltd., Tokyo, Japan

[22] Filed: June 25, 1975

[21] Appl. No.: 590,152

Related U.S. Application Data

[63] Continuation-in-part of Ser. No. 334,727, Feb. 22, 1973, Pat. No. 3,936,505.

[30] Foreign Application Priority Data

Feb. 22, 1972 Japan .............................. 47-17653
Apr. 11, 1972 Japan .............................. 47-35725
Apr. 17, 1972 Japan .............................. 47-37800

[52] U.S. Cl. .......................................... 260/604 R
[51] Int. Cl.² ................... C07C 45/02; C07C 47/20
[58] Field of Search ................................ 260/604 R

[56] References Cited

UNITED STATES PATENTS 3,546,139  12/1970  Young ........................... 260/604 R
3,789,063  1/1974  Lane ............................. 260/604 R

*Primary Examiner*—James O. Thomas, Jr.
*Assistant Examiner*—W. B. Lone
*Attorney, Agent, or Firm*—Oblon, Fisher, Spivak, McClelland & Maier

[57] ABSTRACT

An unsaturated aldehyde having three to four carbon atoms is prepared by reacting the corresponding olefin with molecular oxygen in the vapor phase at a temperature of from 350° to 520° C in the presence of a metal oxide catalyst comprising the metallic components: (a) molybdenum; (b) at least one metal selected from the group consisting of niobium and tantalum; (c) tellurium; and (d) at least one metal selected from the group consisting of alkali metals, copper, arsenic, antimony, iron and nickel.

6 Claims, No Drawings

PROCESS FOR PREPARING UNSATURATED ALDEHYDE HAVING THREE TO FOUR CARBON ATOMS

CROSS-REFERENCE TO RELATED APPLICATIONS

This application is a continuation-in-part of application Ser. No. 334,727, filed Feb. 22, 1973 now U.S. Pat. No. 3,936,505.

BACKGROUND OF THE INVENTION

1. Field of the Invention

This invention relates to a process for preparing unsaturated aldehydes having three to four carbon atoms by oxidizing the corresponding olefin with molecular oxygen. More particularly, this invention relates to a process for preparing methacrolein in high yields by oxidizing isobutylene with molecular oxygen.

2. Description of the Prior Art

Various processes for preparing unsaturated aldehydes by the catalytic vapor phase oxidation of olefins having three to four carbon atoms with molecular oxygen in the presence of various catalysts have been proposed. In most of these processes, acrolein has been advantageously produced from propylene. However, it has been difficult to prepare methacrolein from isobutylene using similar processes. For example, it is known that acrolein can be prepared from propylene in a selectivity of more than 85% and an olefin conversion of 90-95% which is required for industrial production. If the process is used for the preparation of methacrolein from isobutylene, selectivities for methacrolein of up to 50% are obtained which is unsatisfactory for industrial purposes.

Even though propylene and isobutylene are very similar compounds and isobutylene is readily combustible, there is a substantial difference in the oxidative reactivity of the two compounds. However, it is expected that suitable catalysts can be found which exhibit high yields and selectivities for the conversion of isobutylene to methacrolein.

A need, therefore, exists for a catalyst which will promote the oxidative reaction of isobutylene to give methacrolein in high yields and selectivity.

SUMMARY OF THE INVENTION

Accordingly, it is an object of this invention to provide a process for preparing unsaturated aldehydes having three to four carbon atoms in high yield.

It is another object of this invention to provide a process for preparing methacrolein in substantially high yields which have not been attained by conventional processes.

Yet another object of this invention is to provide a process for preparing higher yields of acrolein.

These objects and other objects of this invention as hereinafter will become more readily apparent can be attained by a process for preparing an unsaturated aldehyde having three to four carbon atoms by the oxidation of the corresponding olefin with molecular oxygen in the presence of a metal oxide catalyst containing the metallic components: (a) molybdenum; (b) at least one of niobium and tantalum; (c) tellurium; and (d) at least one metal selected from the group consisting of alkali metals, copper, arsenic, antimony, iron and nickel. The alkali metals include lithium, sodium, potassium, rubidium and cesium and are preferably potassium, cesium, and rubidium.

DESCRIPTION OF THE PREFERRED EMBODIMENTS

The catalysts of this invention have the desired catalytic activity, only when the catalysts contain all of the essential components. If the catalysts lack one or two of the essential components, the activities of these catalysts will be relatively low, which will result in low yields of the desired unsaturated aldehydes, rendering the catalysts unsatisfactory for commercial applications. The preferred catalysts of the invention are characterized by the following empirical formula which, in part, contains 12 molybdenum atoms, $$Mo_{12}-X_a-Te_b-Y_c-O_d \qquad (1)$$

wherein X represents at least one of Nb and Ta; Y represents at least one of alkali metals, Cu, As, Sb, Fe and Ni; $a$ is a number from 0.2 to 9, preferably 0.2–5, most preferably 0.5 to 3; $b$ is a number from 0.2 to 9, preferably 0.5 to 3; $c$ is a number from 0.01 to 9, preferably 0.05 to 5; and $d$ which is determined by the oxidation state of each component, is a number from about 37 to about 103 when each component is in a highly oxidized state.

When the catalysts having the following empirical formula including antimony and alkali metal, are used, the selectivity of the desired unsaturated aldehyde is high and the life of the catalytic activity is advantageously long. Such catalyst has the empirical formula $$Mo_{12}-X_a-Te_b-Sb_e-Y'_{c'}-O_{d'} \qquad (2)$$

wherein Y' represents an alkali metal, $e$ is a number from 0.2–15, preferably 0.5–5; $c'$ is a number from 0.01 to 4, preferably 0.05 to 2, and $d'$ is a number about 37 to 101 when each component is in a highly oxidized state; and X, $a$ and $b$ are defined in the empirical formula (1).

It has been found that the selectivity of the desired unsaturated aldehyde and the life of the catalytic activity are further improved by combining at least one element from the group of Cu, As, Fe and nickel to the catalyst of formula (2). Such catalyst has the empirical formula $$Mo_{12}-X_a-Te_b-Sb_e-Y'_{c'}-Y''_{c''}-O_{d''} \qquad (3)$$

wherein Y'' represents at least one of Cu, As, Fe and Ni; $c''$ is a number from 0.1 to 9, preferably 0.3 to 7; $d''$ is a number about 37 to 115 when each component is in a highly oxidized state; and X, $a$, $b$, $e$ and $c'$ are defined in the empirical formula (2). The catalysts of this invention may be prepared by any one of several methods. Preferably, the catalysts may be prepared by concentrating a solution or a suspension containing the desired components and drying the resulting concentrate. Thereafter, preferably the dried product is calcined at a temperature from 400° to 600° C, especially 450° to 550° C, for about 1 to about 20 hours in air. Then, the calcined product is ground into a mesh size of 35 to 100, which is suitable for use. The prepared catalyst has a specific surface area of 0.1 to 50 m²/g.

In some cases, the catalysts are preferably supported on a suitable carrier, such as silica, silica-containing materials, silicon carbide, alumina and the like, in order to improve the physical properties of the catalysts. The amount of the carrier used is preferably in the range of 30 to 97% by weight based on the weight of the supported catalyst.

The exact chemical structure of the catalysts of the invention is not known. However, it can reasonably be presumed that the catalyst may be a homogeneous mixture of the oxides and/or complex oxides of all the components.

The starting materials of each component used in the preparation of the catalysts are listed as follows: suitable sources of molybdenum include ortho-, meta- or paramolybdic acid, ortho, meta- or paramolybdates, heteromolybdic acid, heteromolybdates, molybdenum oxide and the like. Suitable sources of niobium and tantalum include niobium oxide, niobium hydroxide, niobium oxalate, tantalum oxide, tantalum hydroxide, tantalum oxalate and the like. Suitable sources of an alkali metal, Te, Sb, Cu, As, Fe and Ni include the oxides, nitrates, hydroxides and ammonium salts thereof.

In the preparation of an unsaturated aldehyde having three of four carbon atoms from the corresponding olefin having three or four carbon atoms, the reaction temperature may vary within the range from 350° to 520° C, preferably 430° to 500° C, and the reaction pressure may vary within the range from 1 to 10 atmospheres absolute, preferably 1 to 5 atmospheres absolute. When the reaction pressure is in the upper regions of said range, the reaction temperature may be somewhat lower within the indicated temperature range. The apparent contact time may usually vary from 0.1 to 20 seconds, preferably 0.5 to 5 seconds.

The mole ratio of oxygen to olefin in the feed gas supplied to the reactor usually ranges from 3 : 1 to 1 : 5, especially 3 : 1 to 1 : 1. The oxygen used in the reaction can be any source of molecular oxygen under the reaction conditions with air being the most economical oxygen source. Sometimes, the yield of the desired unsaturated aldehyde is increased by admitting stream to the gaseous reactant mixture. The concentration of steam admitted is preferably in the range of from 5 to 60%, especially 10 to 30%. It is also possible to add an inert gas such as nitrogen or saturated hydrocarbons such as methane, ethane, propane and butane, to said gaseous reactant mixture. Any type of reactor suitable for vapor phase oxidation may be employed in the operation of this invention. Suitable reactors include continuously operating, intermittently operating, solid bed and fluid bed reactors.

In accordance with the process of this invention, the preparation of methacrolein from isobutylene can be successfully conducted on an industrial scale. Therefore, development of new methods of application of methacrolein should be pursued, since methacrolein can be economically and easily prepared.

Having generally described the invention, a more complete understanding can be obtained by reference to certain specific examples, which are intended for purposes of illustration only and are not intended to be limiting unless otherwise specified.

The following definitions apply to olefin conversion and to the selectivity of unsaturated aldehyde. All of the analyses were conducted by means of gas chromatography.

$$\text{Olefin Conversion (\%)} = \frac{\text{Olefin reacted (mole)}}{\text{Olefin fed (mole)}} \times 100$$

$$\text{Selectivity of unsaturated aldehyde} = \frac{\text{Unsaturated aldehyde}}{\text{olfin reacted (mole)}} \times 100$$

The atomic ratio of the metallic components of the catalysts with the exception of the oxygen ratios are shown in the columns of the Tables in the Examples and References.

EXAMPLE 1

A suspension of 2.66 g of niobium oxide ($Nb_2O_5$) in 10 ml of water was added with vigorous stirring to a solution of 42.4 g of ammonium paramolybdenate in 100 ml of water until a slurry was obtained. A 5 ml quantity of nitric acid was diluted with 20 ml of water, and the diluted acid was added to the slurry and heated with stirring. A 5.80 g amount of antimony oxide ($Sb_2O_3$) powder and 6.35 g of tellurium oxide ($TeO_2$) were added to the slurry, heated with stirring, condensed and dried. The resulting cake was dried at 120° C. for 12 hours and then was calcined at 500° C. for 3 hours until a solid oxide having the empirical formula $Mo_{12}Nb_1Te_2Sb_2O_{45.5}$ was obtained.

The solid metal oxide catalyst was crushed and was passed through a sieve to yield a catalyst having a 35-100 mesh particle size. A 2 ml amount of the sieved catalyst was uniformly admixed with 4 ml of silicon carbide having an 80 mesh particle size. A U-shaped, stainless steel reaction tube having an inner diameter of 6 mm was filled with the catalyst. The reaction tube was placed in a molten salt bath at a temperature of 435° C.

A gaseous reactant mixture consisting of 85% nitrogen by volume, 10% oxygen by volume, and 5% isobutylene by volume was passed through the reaction tube with a contact time of 1 second. The results obtained indicated a 71.6% conversion of isobutylene, an 89.5% selectivity of methacrolein and a 6.1% combustion rate ($CO + CO_2$).

EXAMPLES 2-9

The gaseous mixture was reacted in accordance with the process of Example 1, except that metal oxide catalysts having the empirical formulas shown in Table I were prepared by adding a solution or suspension of 4.60 g of arsenic oxide ($As_2O_5$), 0.96 g of lithium hydroxide (LiOH), 1.60 g of sodium hydroxide (NaOH), 2.24 g of potassium hydroxide (KOH), 11.6 g of nickel nitrate ($Ni(NO_3)_2.6H_2O$), 16.1 g of ferric nitrate ($Fe(NO_3)_3.9H_2O$), 9.6 g of cupric nitrate ($Ni(NO_3)_2.6H_2O$), 1.16 g of cesium nitrate in 50 ml of water in place of antimony oxide ($Sb_2O_3$) to the other metal oxide components. The results obtained are shown in Table XIII. It was found that the selectivity of methacrolein was high when these metal oxide catalysts were used.

TABLE I

| Example No. | Catalyst system | Isobutylene Conversion (%) | Methacrolein Selectivity (%) | Combustion ($CO + CO_2$) rate (%) |
|---|---|---|---|---|
| 2 | $Mo_{12}Nb_1Te_2As_2O_{45.5}$ | 71.4 | 82.9 | 14.7 |
| 3 | $Mo_{12}Nb_1Te_2Li_2O_{43.5}$ | 82.1 | 80.3 | 14.8 |

TABLE I-continued

| Example No. | Catalyst system | Isobutylene Conversion (%) | Methacrolein Selectivity (%) | Combustion (CO + CO$_2$) rate (%) |
|---|---|---|---|---|
| 4 | Mo$_{12}$Nb$_1$Te$_2$Na$_2$O$_{43.5}$ | 77.8 | 83.4 | 10.2 |
| 5 | Mo$_{12}$Nb$_1$Te$_2$K$_2$O$_{43.5}$ | 80.1 | 81.9 | 13.0 |
| 6 | Mo$_{12}$Nb$_1$Te$_2$Ni$_2$O$_{44.5}$ | 87.9 | 74.5 | 24.9 |
| 7 | Mo$_{12}$Nb$_1$Te$_2$Fe$_2$O$_{45.5}$ | 96.1 | 75.8 | 20.2 |
| 8 | Mo$_{12}$Nb$_1$Te$_2$Cu$_2$O$_{44.5}$ | 93.5 | 76.6 | 21.4 |
| 9 | Mo$_{12}$Nb$_1$Te$_2$Cs$_{0.3}$O$_{42.6}$ | 75.3 | 91.5 | 6.8 |

EXAMPLES 10–22

The gaseous mixture was reacted in accordance with the process of Example 1 except that metal oxide catalysts having the empirical formulas shown in Table II were used. These catalysts were prepared in accordance with the process of Examples 2–9. The results obtained are shown in Table II.

TABLE II

| Example No. | Catalyst system | Isobutylene Conversion (%) | Methacrolein Selectivity (%) | Combustion rate (CO + CO$_2$) (%) |
|---|---|---|---|---|
| 10 | Mo$_{12}$Nb$_1$Te$_1$Sb$_{0.5}$O$_{42}$ | 78.1 | 80.6 | 13.6 |
| 11 | Mo$_{12}$Nb$_1$Te$_1$Sb$_2$O$_{43.5}$ | 68.0 | 87.0 | 8.3 |
| 12 | Mo$_{12}$Nb$_3$Te$_1$Sb$_2$O$_{48.5}$ | 85.9 | 77.8 | 21.8 |
| 13 | Mo$_{12}$Nb$_1$Te$_1$As$_5$O$_{53}$ | 65.9 | 85.5 | 11.4 |
| 14 | Mo$_{12}$Nb$_3$Te$_2$As$_3$O$_{55}$ | 77.0 | 83.9 | 13.8 |
| 15 | Mo$_{12}$Nb$_1$Te$_2$Li$_{0.5}$O$_{42.8}$ | 80.5 | 79.3 | 14.1 |
| 16 | Mo$_{12}$Nb$_2$Te$_2$Na$_1$O$_{45.5}$ | 85.2 | 80.3 | 13.8 |
| 17 | Mo$_{12}$Nb$_1$Te$_1$Na$_2$O$_{41.5}$ | 83.4 | 82.7 | 10.6 |
| 18 | Mo$_{12}$Nb$_1$Te$_5$K$_{0.5}$O$_{48.8}$ | 77.4 | 84.7 | 10.5 |
| 19 | Mo$_{12}$Nb$_1$Te$_1$Cs$_{0.5}$O$_{40.8}$ | 73.1 | 91.1 | 6.3 |
| 20 | Mo$_{12}$Nb$_1$Te$_2$Cs$_{0.1}$O$_{42.5}$ | 81.9 | 91.0 | 6.5 |
| 21 | Mo$_{12}$Nb$_1$Te$_2$Rb$_{0.5}$O$_{42.8}$ | 78.3 | 89.8 | 8.0 |
| 22 | Mo$_{12}$Nb$_2$Te$_2$Rb$_{0.1}$O$_{45}$ | 83.8 | 89.1 | 8.3 |

EXAMPLES 23–32

The gaseous mixture was reacted in accordance with the process of Example 1, except that metal oxide catalysts having the empirical formulas shown in Table III were used. These catalysts were prepared in accordance with the process of Examples 2–9. The results obtained are shown in Table III.

TABLE III

| Example No. | Catalyst system | Isobutylene Conversion (%) | Methacrolein Selectivity (%) | Combustion rate (CO + CO$_2$) (%) |
|---|---|---|---|---|
| 23 | Mo$_{12}$Nb$_1$Te$_2$Fe$_{0.5}$O$_{43.3}$ | 88.4 | 78.2 | 16.1 |
| 24 | Mo$_{12}$Nb$_1$Te$_5$Fe$_5$Sb$_1$O$_{57.5}$ | 90.1 | 74.2 | 20.9 |
| 25 | Mo$_{12}$Nb$_{0.5}$Te$_2$Fe$_2$O$_{44.3}$ | 88.0 | 76.5 | 21.9 |
| 26 | Mo$_{12}$Nb$_1$Te$_1$Cu$_1$O$_{41.5}$ | 91.7 | 78.0 | 20.9 |
| 27 | Mo$_{12}$Nb$_3$Te$_4$Cu$_3$O$_{54.5}$ | 89.1 | 72.6 | 25.3 |
| 28 | Mo$_{12}$Nb$_1$Te$_2$Sb$_2$Cu$_2$O$_{49.5}$ | 87.2 | 82.6 | 13.0 |
| 29 | Mo$_{12}$Nb$_1$Te$_2$Sb$_2$Fe$_7$O$_{58}$ | 96.3 | 78.2 | 17.5 |
| 30 | Mo$_{12}$Nb$_1$Te$_2$Sb$_2$Ni$_5$O$_{52.5}$ | 87.7 | 82.8 | 16.0 |
| 31 | Mo$_{12}$Nb$_1$Te$_2$Sb$_2$Cu$_2$Fe$_2$O$_{52.5}$ | 90.3 | 81.6 | 16.3 |
| 32 | Mo$_{12}$Nb$_1$Te$_2$Sb$_2$Cu$_2$Ni$_2$O$_{51.5}$ | 86 | 80.9 | 16.1 |

EXAMPLE 33

The gaseous mixture was reacted in accordance with the process of Example 1, except that the metal oxide catalyst used having the empirical formula Mo$_{12}$Ta$_1$Te$_2$Sb$_2$O$_{45.5}$ were prepared with 4.42 g of tantalum oxide (Ta$_2$O$_5$) instead of niobium oxide. The results obtained indicated a 73.2% conversion of isobutylene, an 85.9% selectivity of methacrolein and a 13.3% combustion rate.

EXAMPLES 34–39

The gaseous mixture was reacted in accordance with the process of Example 1, except that metal oxide catalysts having the empirical formulas shown in Table IV were used. These catalysts were prepared by using 4.42 g of tantalum oxide instead of niobium oxide in accordance with the process of Example 1. The results obtained are shown in Table IV.

TABLE IV

| Example No. | Catalyst system | Isobutylene Conversion (%) | Methacrolein Selectivity (%) | Combustion rate (CO + CO$_2$) (%) |
|---|---|---|---|---|
| 34 | Mo$_{12}$Ta$_1$Te$_2$As$_3$O$_{55}$ | 74.3 | 83.7 | 14.4 |
| 35 | Mo$_{12}$Ta$_1$Te$_1$Na$_2$O$_{41.5}$ | 77.1 | 81.1 | 17.6 |
| 36 | Mo$_{12}$Ta$_1$Te$_2$Cu$_2$O$_{44.5}$ | 91.5 | 70.0 | 21.2 |
| 37 | Mo$_{12}$Ta$_{0.5}$Nb$_{0.5}$Te$_2$Cu$_2$O$_{43.5}$ | 86.3 | 75.4 | 20.9 |
| 38 | Mo$_{12}$Ta$_1$Te$_2$Sb$_2$Fe$_2$O$_{43.5}$ | 92.8 | 76.4 | 20.7 |
| 39 | Mo$_{12}$Ta$_1$Te$_2$Sb$_2$Ni$_2$O$_{47.5}$ | 89.5 | 77.3 | 19.2 |

COMPARISON EXAMPLES 1-8

The gaseous mixture was reacted in accordance with the process of Example 1, except that the metal oxide catalysts having the empirical formulas shown in Table V were used. These catalysts were prepared in accordance with the process of Examples 1-39. The results obtained are given in Table V.

TABLE V

| Comparison Example No. | Catalyst system | Isobutylene Conversion (%) | Methacrolein Selectivity (%) | Combustion rate $(CO + CO_2)$ (%) |
|---|---|---|---|---|
| 1 | $Mo_{12}Nb_1Te_2Sn_2O_{46.5}$ | 77.3 | 52.8 | 37.2 |
| 2 | $Mo_{12}Nb_1Te_2Pd_2O_{43}$ | 62.1 | 51.7 | 48.0 |
| 3 | $Mo_{12}Nb_1Te_2P_1O_{44}$ | 17.9 | 50.4 | 51.4 |
| 4 | $Mo_{12}Te_2Ce_2O_{44}$ | 48.5 | 75.2 | 29.7 |
| 5 | $Mo_{12}Te_2Co_2O_{42}$ | 25.3 | 86.0 | 12.6 |
| 6 | $Mo_{12}Nb_1Fe_1Sb_2O_{43}$ | 46.0 | 51.3 | 45.1 |
| 7 | $Mo_{12}Nb_1Te_2O_{42.5}$ | 82.3 | 70.5 | 23.0 |
| 8 | $Mo_{12}Ta_1Te_2O_{42.5}$ | 81.8 | 67.3 | 25.6 |

EXAMPLE 40

The gaseous mixture was reacted in accordance with the process of Example 1, except that 6 ml of a metal oxide catalyst having the empirical formula $Mo_{12}Nb_1Te_2Sb_2O_{45.5}$ was used without the presence of silicon carbide. The contact time of the gas mixture was 3 seconds. The results obtained indicated a 94.5% conversion of isobutylene, an 89.1% selectivity of methacrolein and a 6.9% combustion rate.

EXAMPLE 41

The gaseous mixture was reacted in accordance with the process of Example 1, except that 6 ml of a metal oxide catalyst having the empirical formula $Mo_{12}Nb_1Te_2Fe_2O_{45.5}$ was used, without the presence of silicon carbide. The contact time for the gas mixture was 3 seconds at a temperature of 395° C in a molten salt bath. The results obtained indicated a 96.7% conversion of isobutylene, a 74.5% selectivity of methacrolein and an 18.5% combustion rate.

EXAMPLES 42-48

The gaseous mixture was reacted in accordance with the process of Example 1, except that propylene was used instead of isobutylene. In addition, the catalysts shown in Table VI were used at a temperature of 400° C in the molten salt bath. The results obtained are shown in Table VI.

TABLE VI

| Example No. | Catalyst system | Propylene Conversion (%) | Acrolein Selectivity (%) | Combustion rate $(CO + CO_2)$ (%) |
|---|---|---|---|---|
| 42 | $Mo_{12}Nb_1Te_2Sb_2O_{45.5}$ | 85.0 | 91.6 | 4.2 |
| 43 | $Mo_{12}Nb_1Te_2Fe_2O_{45.5}$ | 98.8 | 83.6 | 12.5 |
| 44 | $Mo_{12}Nb_1Te_2Cs_{0.5}O_{42.8}$ | 89.2 | 93.8 | 6.0 |
| 45 | $Mo_{12}Nb_1Te_2Cu_2O_{44.5}$ | 96.2 | 84.9 | 11.0 |
| 46 | $Mo_{12}Ta_1Te_2Sb_2O_{45.5}$ | 87.0 | 88.4 | 10.1 |
| 47 | $Mo_{12}Nb_{0.5}Ta_{0.5}Te_2Na_1O_{43}$ | 95.2 | 85.1 | 12.8 |
| 48 | $Mo_{12}Nb_1Ta_{0.5}Te_5As_2O_{54.8}$ | 93.8 | 87.2 | 11.0 |

EXAMPLE 49

A 2.66 g amount of niobium oxide ($Nb_2O_5$) and 5.80 g of antimony oxide ($As_2O_3$) were added to a solution of 42.4 g of $(NH_4)_6Mo_7O_{24}\cdot 4H_2O$ in 100 ml of water, and then a mixture of 20 ml of nitric acid and 60 ml of water was added to the solution with stirring for 1 hour while heating to obtain a slurry. A 6.35 g amount of $TeO_2$ and a solution of 2.02 g of potassium nitrate in 20 ml of water were sequentially added to the slurry. The mixture was heated with stirring to evaporate most of the water. A 240 g amount of silicon-carbide (10-20 mesh) was admixed with the product and the mixture was dried at 120° C for 12 hours and then calcined at 520° C for 5 hours to obtain a catalyst of about 20% $Mo_{12}Nb_1Te_2Sb_2K_1O_{46}$ supported on silicon-carbide carrier.

A 24 ml of the catalyst was filled in a U-shaped stainless steel reaction tube having an inner diameter of 8 mm. The reaction tube was dipped into a molten salt bath at 440° C and a gaseous reactant mixture consisting of 85% nitrogen by volume, 10% oxygen by volume and 5% isobutylene by volume was passed through the reaction tube with a contact time of 10 seconds (as NTP).

As a result, the conversion of isobutylene was 90.5%; the selectivity of methacrolein was 86.6% and the combustion rate was 9.5%. When the reaction was continued for 500 hours, the conversion of isobutylene was 85.8% and the selectivity of methacrolein was 87.0%.

EXAMPLE 50

The process of Example 49 was repeated, except that 4.42 grams of tantalum oxide powder ($Ta_2O_5$) were used instead of $Nb_2O_5$ to obtain a catalyst of about 20% $Mo_{12}Ta_1Te_2Sb_2K_1O_{46}$ supported on the silicon-carbide carrier. The reaction of Example 49 was repeated using the above resulting catalyst. As a result, the conversion of isobutylene was 94.2%, the selectivity of methacrolein was 84.3% and the combustion rate was 12.0%. When the reaction was continued for 500 hours, the conversion of isobutylene was 89.0% and the selectivity of methacrolein was 82.7%.

EXAMPLES 51-61

The process of Example 50 was repeated, except that the amount of the alkali metal compound was varied in the catalysts obtained as shown in Table VII. The reaction of Example 49 was repeated, except that the alkali metal containing catalysts were used. The results are shown in Table VII.

TABLE VII

| Example No. | Catalyst system | Isobutylene Conversion (%) | Methacrolein Selectivity (%) | Combustion rate (CO + CO$_2$) (%) |
|---|---|---|---|---|
| 52 | Mo$_{12}$Nb$_1$Te$_2$Sb$_2$Li$_2$O$_{46.5}$ | 85.1 | 87.0 | 10.1 |
| 52 | Mo$_{12}$Nb$_1$Te$_2$Sb$_2$Na$_2$O$_{46.5}$ | 79.4 | 87.1 | 9.9 |
| 53 | Mo$_{12}$Nb$_1$Te$_2$Sb$_2$K$_{0.3}$O$_{45.7}$ | 92.3 | 85.2 | 10.0 |
| 54 | Mo$_{12}$Nb$_1$Te$_2$Sb$_2$K$_2$O$_{46.5}$ | 75.8 | 90.1 | 7.1 |
| 55 | Mo$_{12}$Nb$_1$Te$_2$Sb$_2$K$_4$O$_{47.5}$ | 50.3 | 89.0 | 8.8 |
| 56 | Mo$_{12}$Nb$_1$Te$_2$Sb$_2$Rb$_{0.3}$O$_{45.8}$ | 90.6 | 86.1 | 10.5 |
| 57 | Mo$_{12}$Nb$_1$Te$_2$Sb$_2$Cs$_{0.1}$O$_{45.6}$ | 90.7 | 86.2 | 10.4 |
| 58 | Mo$_{12}$Nb$_1$Te$_2$Sb$_2$Cs$_{0.5}$O$_{45.8}$ | 82.0 | 90.7 | 7.5 |
| 59 | Mo$_{12}$Nb$_1$Te$_2$Sb$_2$Cs$_1$O$_{46}$ | 70.8 | 88.9 | 8.8 |
| 60 | Mo$_{12}$Ta$_1$Te$_2$Sb$_2$K$_{0.3}$O$_{45.7}$ | 92.7 | 85.3 | 10.8 |
| 61 | Mo$_{12}$Ta$_1$Te$_2$Sb$_2$Cs$_{0.3}$O$_{45.7}$ | 85.1 | 87.1 | 10.3 |

EXAMPLES 62-68

The catalysts having the empirical formula shown in Table VIII were prepared in accordance with the process of Examples 49-51, except that Cu, Fe or Ni were added in the following form:

Cu: 19.3 g of Cu (NO$_3$)$_2$.3H$_2$O or a solution of 9.7 g of Cu(NO$_3$)$_2$.3H$_2$O in 100 ml of water Fe: Solution of 16.2 g of Fe(NO$_3$)$_3$.9H$_2$O in 100 ml of water Ni: Solution of 11.2 g of Ni(NO$_3$)$_2$.6H$_2$O in 100 ml of water The reaction of Example 49 was repeated, except that the above catalysts were used in the reaction at 420° C with a contact time of 5 seconds.

The results are shown in Table VIII.

TABLE VIII

| Example No. | Catalyst system | Isobutylene Conversion (%) | Methacrolein Selectivity (%) | Combustion rate (CO + CO$_2$) (%) |
|---|---|---|---|---|
| 62 | Mo$_{12}$Nb$_1$Te$_2$Sb$_2$K$_1$Ni$_2$O$_{48}$ | 88.7 | 85.7 | 9.8 |
| 63 | Mo$_{12}$Nb$_1$Te$_2$Sb$_2$K$_1$Cu$_4$O$_{50}$ | 91.0 | 83.4 | 12.8 |
| 64 | Mo$_{12}$Nb$_1$Te$_2$Sb$_2$Li$_2$Cu$_2$O$_{48.5}$ | 93.8 | 82.0 | 15.0 |
| 65 | Mo$_{12}$Nb$_1$Te$_2$Sb$_2$Na$_1$Fe$_2$O$_{49}$ | 93.7 | 81.5 | 15.1 |
| 66 | Mo$_{12}$Nb$_1$Te$_2$Sb$_2$Cs$_{0.3}$Ni$_2$O$_{47.7}$ | 91.3 | 82.8 | 13.9 |
| 67 | Mo$_{12}$Ta$_1$Te$_2$Sb$_2$Cs$_{0.3}$Cu$_2$O$_{47.7}$ | 91.1 | 83.9 | 15.7 |
| 68 | Mo$_{12}$Nb$_1$Te$_2$Sb$_2$K$_1$Cu$_2$Fe$_2$O$_{51}$ | 97.0 | 80.2 | 16.0 |

EXAMPLE 69

The reaction of Example 49 was repeated, except that propylene was used instead of isobutylene and the reaction was conducted at 445° C.

As a result, the conversion of propylene was 92.3%, the selectivity of acrolein was 89.7% and the combustion rate was 7.6%.

Having now fully described the invention, it will be apparent to one of ordinary skill in the art that many changes and modifications can be made thereto without departing from the spirit or scope of the invention as set forth herein.

What is claimed and intended to be covered by Letters Patent is:

1. A process for preparing an unsaturated aldehyde having three to four carbon atoms, which comprises:
reacting the corresponding olefin with molecular oxygen in a mole ratio of oxygen to olefin ranging from 3 : 1 to 1 : 5 in the vapor phase at a temperature of from 350° to 520° C and a pressure of 1 to 10 atms. in the presence of a metal oxide catalyst having the formula:

$$Mo_{12}-X_a-Te_b-Y_c-O_d$$

wherein X is Nb or Ta; Y is at least one metal selected from the group consisting of alkali metals, Cu, As, Sb, Fe and Ni; $a$ is 0.2 to 9; $b$ is 0.2 to 9; $c$ is 0.01 to 9; $d$ is determined by the oxidation states of the other components.

2. The process of claim 1, wherein the temperature of reaction is 430° to 450° C.

3. The process of claim 1, wherein the pressure of the reaction ranges from 1 to 5 atmospheres.

4. The process of claim 1, wherein the mole ratio of oxygen to olefin is from 3 : 1 to 1 : 1.

5. A process for preparing an unsaturated aldehyde having three to four carbon atoms, which comprises:
reacting the corresponding olefin with molecular oxygen in a mole ratio of oxygen to olefin ranging from 3 : 1 to 1 : 5 in the vapor phase at a temperature of from 350° to 520° C and a pressure of 1 to 10 atms. in the presence of a metal oxide catalyst having the formula:

$$Mo_{12}-X_a-Te_b Sb_e-Y'_{c'} -O_{d'}$$

wherein Y' is an alkali metal; $c'$ is 0.01 to 4; $e$ is 0.2 to 15; $d'$ is determined by the oxidation states of the other components and X, $a$ and $b$ are the same as in claim 1.

6. A process for preparing an unsaturated aldehyde having three to four carbon atoms, which comprises:
reacting the corresponding olefin with molecular oxygen in a mole ratio of oxygen to olefin ranging from 3 : 1 to 1 : 5 in the vapor phase at a temperature of from 350° to 520° C and a pressure of 1 to 10 atms. in the presence of a metal oxide catalyst having the formula:

$$Mo_{12}-X_a-Te_b-Sb_e-Y'_{c'} -Y''_{c''} -O_{d''}$$

wherein Y'' is at least one metal selected from the group consisting of Cu, As, Fe and Ni, $c''$ is 0.1 to 9; $d''$ is determined by the oxidation states of the other components; and X, $a$, $b$, $c'$ and $e$ are the same as in claim 2.

* * * * *